United States Patent [19]

Bitonti et al.

[11] Patent Number: 5,134,168

[45] Date of Patent: Jul. 28, 1992

[54] PHENOXY AND PHENYLTHIO, AMINO SUBSTITUTED BENZOCYCLOALKANE DERIVATIVES IN THE TREATMENT AND PREVENTION OF DRUG-RESISTANT PROTOZOAL INFECTIONS

[75] Inventors: Alan J. Bitonti, Maineville; Jules Freedman, Cincinnati, both of Ohio

[73] Assignee: Merrell Dow Pharmaceuticals Inc., Cincinnati, Ohio

[21] Appl. No.: 668,390

[22] Filed: Mar. 13, 1991

Related U.S. Application Data

[63] Continuation of Ser. No. 278,689, Dec. 1, 1988, abandoned.

[51] Int. Cl.[5] .................. A61K 31/135; A61K 31/335; A61K 31/36
[52] U.S. Cl. .................................... 514/655; 514/657; 514/463; 514/464
[58] Field of Search ................ 514/657, 655, 463, 464

[56] References Cited

U.S. PATENT DOCUMENTS 4,177,292 12/1979 Nedelec et al. ..................... 514/657

OTHER PUBLICATIONS

Hewlett, E. L. and Pearson, R. D., *Science*, vol. 230 pp. 1063-1064 (1985).
Zilberstein, D. and Dwyer, D. M., *Science:* 226, 977-9 (1984).
P. Dutta et al., *Clinical Pharmacology:* 279 (1986).
T. B. Geary, et al., *Antimicrobial Agents and Chemotherapy*, pp. 785-788 (1986).
L. W. Scheibel et al., *Proc. Natl. Acad. Sci., USA*, vol. 84, pp. 7310-7314, (1987).

*Primary Examiner*—Jerome D. Goldberg
*Attorney, Agent, or Firm*—Stephen L. Nesbitt

[57] ABSTRACT

Drug-resistant protozoal infection, particularly, drug-resistant malarial infection in humans, can be effectively treated with standard antiprotozoal agents if administered in conjunction with a phenoxyamino-substituted benzocycloalkane derivative.

13 Claims, 1 Drawing Sheet

FIG. 1

PHENOXY AND PHENYLTHIO, AMINO SUBSTITUTED BENZOCYCLOALKANE DERIVATIVES IN THE TREATMENT AND PREVENTION OF DRUG-RESISTANT PROTOZOAL INFECTIONS

CROSS-REFERENCE TO RELATED APPLICATION

This is a continuation of application Ser. No. 07/278,689 filed Dec. 1, 1988, now abandoned.

This invention relates to the use of certain phenoxy and phenylthio, amino substituted benzocycloalkane derivatives in the treatment and prevention of drug-resistant malaria and in the treatment and prevention of other drug-resistant protozoal infections.

BACKGROUND OF THE INVENTION

Malaria remains a significant health threat to humans despite massive international attempts to eradicate the disease. Over 200 million people are said to have malaria and over one million deaths per year are associated with malaria in Africa alone. In many of the endemic areas, local supply of food is quite limited, a problem which is greatly aggravated by the presence of protozoal infections in cattle and other farm animals.

Malaria is a disease of warm blooded animals caused by infection with a parasite of the genus Plasmodium. Four species, P. vivax, P. falciparum, P. malariae, and P. ovale, are known to infect humans. The parasite is transmitted to humans by the bite of Anopheles mosquitoes. Subsequent to humans by the bite of Anopheles mosquitoes. Subsequent to mosquito bite, the parasite rapidly invades the blood cells of the victim and after a incubation period, generally lasting about 10 to 14 days, symptoms, consisting of chills, fever, headache, muscle pains, spenomegaly, and anemia, appear. This incubation period may be prolonged for many weeks and onset can be quite insidious. Red blood cells are at first altered and later destroyed by the infection. After an acute episode, the victim may be reinfected by the parasite which persists in the liver.

Drug therapy utilizing quinine, chloroquine, amodiaquine, primaquine, and other agents has been the mainstay of therapy against malaria and diseases caused by infection by other protozoa such as various species of Leishmaniasis and Trypanosomiasis. However, drug-resistant strains of protozoa have developed and in some cases strains are resistant to many or all of the current therapeutic agents. In particular, P. falciparum malaria is quite prone to exhibit single and even multiple drug-resistance. While new agents are continually developed and introduced, resistance to such new agents also quickly develops. For example mefloquine-resistant malaria was reported even before mefloquine licensure was completed. There is, thus, an urgent need for antimalarial and antiprotozoal agents which can be used in the treatment of drug-resistant malaria and other protozoal diseases.

Recently it was reported that the antidepressant compounds imipramine and amitryptyline suppress P. falciparum growth by virtue of the ability of these agents to interfere with riboflavin metabolism. While scientifically interesting, the practical use of imipramine and amitryptyline and other antidepressant compounds in the treatment of malaria would seem unlikely because of the lethal doses required to produce the anti-malarial effect in humans. Applicants have now discovered that certain antidepressant phenoxy and phenylthio, amino substituted benzocycloalkane derivatives, when administered in subtoxic doses in conjunction with standard antimalarial agents, are highly effective in treating and preventing drug-resistant malarial and other drug-resistant protozoal infections.

SUMMARY OF THE INVENTION

Applicants have found that certain phenoxy and phenylthio, amino substituted benzocycloalkane derivatives of formula 1 wherein
$R_1$ is a $C_1$–$C_3$ alkylene,
n, p and q are each independently 0, 1 or 2,
Y and X are each independently lower alkyl, lower alkoxy, hydroxy, CF, halogeno or when p or q are 2 and each of the Y or each of the X groups are on adjacent aryl carbon atoms, both of the X or both of the Y groups can be taken together to form a methylenedioxy moiety,
$R_2$ and $R_3$ are each independently hydrogen, or lower alkyl, and
$R_4$ is an oxy or thio,
or a pharmaceutically acceptable salt thereof when administered conjunctively with an antiprotozoal agent are useful in the treatment of individuals suffering from and prevention of drug-resistant malaria and other drug-resistant protozoal infections.

Figure 1:
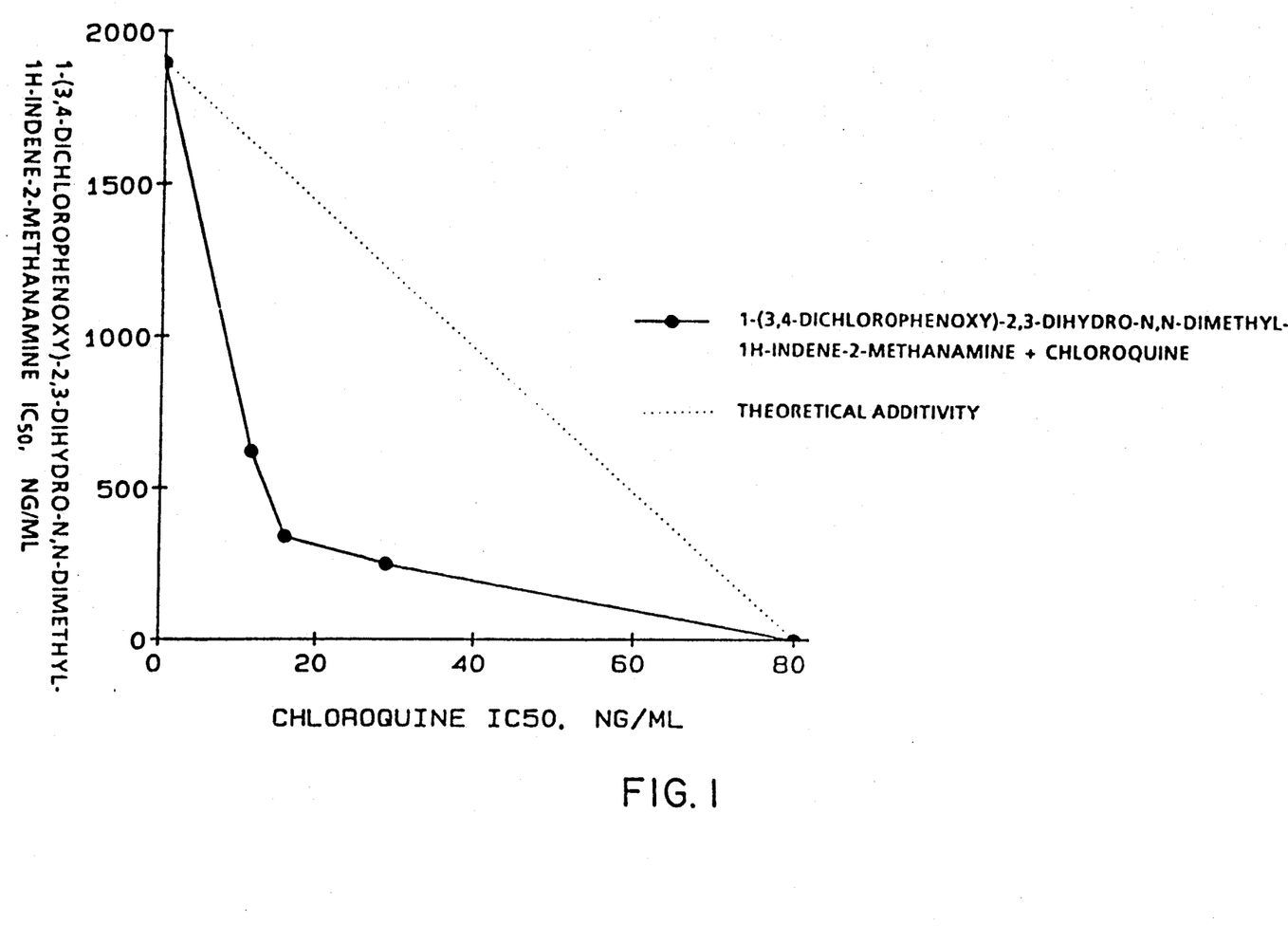
FIG. 1 illustrates the synergism of 1-(3,4-dichlorophenoxy)-2,3-dihydro-N,N-dimethyl-1H-Indene-2-methanamine and chloroquine against chloroquine-resistant P. falciparum (FCR3). Isobologram analysis was carried out according to the method of Martin, et al., (1987) Science 235, 899–901 and Berenbaum, (1978) Journal of Infectious Diseases 137, 122–130. Drug synergy in this test is demonstrated when a test curve (solid line, 1-(3,4-dichlorophenoxy)-2,3-dihydro-N,N-dimethyl-1H-Indene-2-methanamine+chloroquine) falls to the left of the theoretical additivity line as is the case with the 1-(3,4-dichlorophenoxy)-2,3-dihydro-N,N-dimethyl-1H-Indene-2-methanamine+chloroquine curve. The X-axis is the IC$_{50}$ concentration of drug which inhibits hypoxanthine incorporation by 50%) of chloroquine in the absence or presence of 1-(3,4-dichlorophenoxy)-2,3-dihydro-N,N-dimethyl-1H-Indene-2-methanamine while the Y-axis is the IC$_{50}$ for 1-(3,4-dichlorophenoxy)-2,3-dihydro-N,N-dimethyl-1H-Indene-2-methanamine in the absence or presence of chloroquine. The more highly synergistic a combination is, the closer to the origin the points will fall. The combination of 1-(3,4-dichlorophenoxy)-2,3-dihydro-N,N-dimethyl-1H-Indene-2-methanamine and chloroquine is shown to be highly synergistic.

DETAILED DESCRIPTION OF THE INVENTION $R_1$ is a divalent alkylene group comprised of 1 to 3 carbon atoms of straight or branched chain configuration including, for example, $-CH_2-$, $-CH_2CH_2-$, $-CH_2CH_2CH_2-$, $-C(CH_3)_2-$, and $-CH(CH_3)CH_2-$. Where $R_1$ is $-CH_2-$, the compounds of formula (1) are phenoxy and phenylthio indanamine derivatives; where $R_1$ is $-CH_2CH_2-$, the compounds of formula (1) are phenoxy and phenylthio-1,2,3,4-tetrahydronapthylamine derivatives; where $R_1$ is $-CH_2CH_2CH_2-$, the compounds of formula (1) are phenoxy and phenylthio-5,6,7,8-benzocycloheptenamine derivatives.

The phenoxy and phenylthio moieties of compounds of formula (1) can be mono- or di-substituted at any feasible position(s) in the ring (when q is 1 or 2, respectively) or it can be unsubstituted (when q is O). X is independently chosen each time it is taken so that when q is 2 the phenoxy and phenylthio moieties is di-substituted with the same or different substituents. Likewise, the fused-ring moiety can be mono- or di-substituted at any of the 4, 5, 6, or 7 position(s) (when p is 1 or 2, respectively) or it can be unsubstituted (when p is O). Y is independently chosen each time it is taken so that when p is 2 the fused-ring moiety is di-substituted with the same or different substituents.

As used herein, the term "lower alkyl" refers to an alkyl group comprised of 1 to 6 carbon atoms in straight, branched, or cyclic configuration. The term "lower alkoxy" refers to a lower alkyl group substituted with a single oxygen atom which is attached to the appropriate aryl carbon. The term "halogeno" refers to a fluoro, chloro, bromo or iodo substituent. The term "methylenedioxy" refers to a $-O-CH_2-O-$ moiety attached to adjacent aryl carbon atoms.

Compounds wherein $R_2$ and/or $R_3$ are $CO_2Me$ or $CO_2Et$, i.e., the methyl or ethyl ester of a carboxy group, are novel intermediates useful in the preparation of compounds of the formula (1). These esters can be made by utilizing procedures analogous to those described below for compounds of the formula (1) and by utilizing standard procedures well known and appreciated in the art.

Compounds of the formula (1) can be employed as free amines or as acid addition salts thereof The term "acid addition salts" encompasses both organic and inorganic acid addition salts including, for example, those prepared from acids such as hydrochloric, oxalic, and the like. For example, compounds of the formula (1) wherein X or Y is $CF_3$ can be converted to the hydrochloric acid addition salt using conventional methods well known in the art.

As will be recognized and appreciated by those skilled in the art, the compounds of formula (1) can exist in a CIS or TRANS stereoisomeric form with respect to the phenoxy and phenylthio moieties and the amine moiety. It is understood that the present invention encompasses both the CIS or TRANS forms individually and mixtures thereof. Further, it is apparent to those skilled in the art that the compounds of formula (1) have two chiral centers (positions 1 and 2) and can exhibit optical activity. Unless specifically indicated, a compound of formula (1) means the substantially pure stereoisomers as well as mixtures including the racemic modification thereof.

In general, the compounds of formula (1) may be prepared by chemical reactions analogously known in the art, the choice of any specific route of preparation being dependent upon a variety of factors. For example, general availability and cost of the reactants, applicability of certain generalized reactions to specific compounds, and so forth, are all factors which are fully understood by those of ordinary skill in the art and all contribute to the choice of synthesis in the preparation of any specific compound embraced by formula (1). In preparing these compounds, standard procedures and techniques which are well known and appreciated by those of ordinary skill in the art are utilized.

For example, compounds of the formula (1) can conveniently be made according to the general synthetic route outlined in Scheme A.

Scheme A*

Scheme A*

*The $Y_p$, $X_q$, $R_1$, $R_2$, $R_3$ substituents are as previously defined.

In general, compounds of the formula (1) wherein $R_4$ is oxy can be prepared by reacting the appropriately substituted amino ketone (2) with L-Selectride ® (lithium tri-O-isobutyl borohydride available from Aldrich) to give the amino alcohol (3). This generally results in the CIS isomer in substantially pure form. The sodium derivative of the amino alcohol (3) which is formed by reacting (3) with sodium hydride (NaH) in dimethylsulfoxide (DMSO) is further reacted with the appropriately substituted aryl fluoride (F—ArXq) in the presence of DMSO to give the corresponding compound of the formula (1). Again this generally results in the CIS isomer in substantially pure form or in a mixture of the CIS and TRANS isomers.

Alternatively, compounds of the formula (1) wherein $R_4$ is oxy can be prepared by reacting the appropriately substituted amino ketone (2) with sodium borohydride (NaBH$_4$) which gives the amino alcohol (4) in substantially pure TRANS isomeric form. The compounds of the formula (1) can then be formed by reacting the sodium derivative of the amino alcohol (4) with the appropriately substituted aryl fluoride as described above. This procedure generally results in the TRANS isomer in substantially pure form or in a mixture of the CIS and TRANS isomers. In the alternative, the amino alcohol (4) can be reacted with the appropriately substituted phenol (HO—ArX) in the presence of triphenyl phosphine ($\phi_3$P) and diethylazodicarboxylate (EtOOCN=NCOOEt). This procedure generally yields mixtures of the CIS and TRANS isomers of the formula (1).

The compounds of formula (1) wherein $R_4$ is thio can be prepared by reaction of a compound of either formula (3) or formula (4) with diphenyl disulfide and tri-(n-butyl)phosphine in a solvent such as benzene. The reaction can be performed at from about 0° C. to about 65° C. conveniently at room temperature. Depending on various factors, the reaction will be substantially complete in from about 6 hours to about 24 hours, with 12 hours being typical. The product can be isolated by solvent removal. Purification can be achieved by, for example, flash chromatography on silica gel eluting with methanolethyl acetate (5:95). This reaction typically proceeds with inversion of stereochemistry, thus the formula (2) compound will yield predominantly TRANS and the formula (4) compound will yield predominantly CIS product.

Where it is desired to resolve and isolate the CIS or TRANS stereoisomeric forms of a compound of the formula (1) from a mixture thereof, this resolution can be effected by standard procedures and techniques as are well known and appreciated in the art.

The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the sulfonic acids such as methane sulfonic acid and 2-hydroxyethane sulfonic acid. Either the mono- or the di-acid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution.

The term "patients" as used herein means those warm-blooded animals, such as cattle, sheep, goats, swine, and primates including humans, manifesting diseases caused by drug-resistant protozoal infections. The most important use of the present invention is its use in the treatment of drug-resistant protozoal infections in humans.

As used herein, the term "protozoal infections" means those protozoal infections of warm-blooded animals by such genera as *Plasmodium* (including such species as *vivax, malariae, ovale, falciparum, knowlesi, berghei, vinckei, chabaudi, gallinaceum,* and *lophurae*), *Leishmania* (including such species as *donovani, tropica, braziliensis,* and *mexicana*), *Trypanosoma* (including such species as *cruzi*), Babesiosis, and Theileria species. The most important use contemplated for the present invention is its use in the treatment and prevention of drug-resistant Plasmodium infections, especially malarial infections of drug-resistant strains of *P. falciparum*, in humans.

The term "drug-resistant protozoal infections" means those protozoal infections in which the infecting strain of protozoa is either completely or substantially refractory to therapy with existing antiprotozoal agents or combinations of antiprotozoal agents. The term "drug-resistant malaria" means a malarial infection, particularly of malaria resulting from infection by *P. falciparum* in humans, which are substantially not responsive to treatment with existing therapeutic agents such as quinine, chloroquine, amodiaquine, primaquine, or mefloquine.

Therapeutic and prophylactic agents used in treating and preventing protozoal infections of warm blooded animals and those antiprotozoal agents used in the combination therapy of this invention include any therapeutic agent used in treating or preventing non-drug-resistant protozoal infections and those therapeutic and prophylactic agents currently used in treating and preventing drug-resistant protozoal infections such as mefloquine. As used herein, the terms "antiprotozoal agent" and "antimalarial agent" specifically do not include the compounds of formula 1. Examples of antiprotozoal agents used in treating and preventing malarial infections are various quinoline derivatives such as quinine, chloroquine, primaquine, sulfadoxine, mefloquine, and pyrimethamine. Examples of antiprotozoal agents used in treating Leishmaniasis infections are various pentavalent antimony compounds such as sodium stibogluconate, amphotericin B, and pentamidine isethionate. Examples of antiprotozoal agents used in treating Trypanosomiasis infections are nifurtimox, suramin, melarsoprol, alpha-difluoromethylornithine (DFMO), and pentamidine. Various salts of these agents may also be employed and combinations of these various agents are routinely utilized.

The term "conjunctive therapy" as used herein contemplates the administration of a formula 1 compound immediately prior to, concomitantly with, or subsequent to treatment with the antiprotozoal agent or agents whether to treat or prevent such an infection. Applicants contemplate that the phenoxyamino substituted benzocycloalkane derivatives of this invention may be formulated into a single dosage form together with the antiprotozoal agent; however, such a combination dosage form is not required in order to practice the method of this invention. Rather, because the antiprotozoal agents are widely available in separate dosage forms, applicants expect that patients will be treated using such dosage forms together with a separate dosage form containing a compound of formula (1). Typically, treatment of a patient infected with a drug-resistant protozoa, requires doses of the antiprotozoal agent or agents many times the normal dosage, and such therapy is heroic in nature, i.e., in an effort to save the life of the patient, doses of antiprotozoal agents normally regarded as "overdosages" are used and symptomatic relief of overdosage symptoms are tended to on an individual basis. While the conjunctive therapy of this invention will provide for use of less antiprotozoal agent than would be possible in the absence of the formula 1 compound, applicants contemplate that the dose of antiprotozoal agent employed in the method of this invention will be essentially that dose which would be employed in the absence of the formula 1 compound when used to treat a non drug-resistant protozoal infection. Rather than decreasing the dose of antiprotozoal agent required, the conjunctive therapy of this invention will provide for treatment of protozoal infections which would otherwise not be adequately treated in the absence of a formula 1 compound. In fact, it is the very gist of applicants' discovery that protozoal infections which are not responsive to therapy with standard antiprotozoal agents, become sensitive to such therapy when administered in conjunction with a compound of formula (1).

A therapeutically or prophylactically effective amount of a compound of formula (1) varies from about 0.1 milligrams per kilogram of body weight per day (mg/kg/day) to about 100 mg/kg/day. Preferred amounts are expected to vary from about 1 to about 10 mg/kg/day.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Pharmaceutical compositions of the antiprotozoal agents are widely available and can be used in the practice of this invention. Dosage forms of the formula (1) compounds of this invention will contain from 5 to 250 mg and are to be administered to a human patient from 1 to 3 or 4 times daily, as required. Such dosage forms and frequency of administration are suitable for use in practicing the method of this invention. Pharmaceutical compositions of antimalarial agents such as chloroquine and compositions of other antiprotozoal agents are also widely available and can be used in the practice of the method of this invention.

The ability of the compounds of formula 1 to treat drug-resistant protozoal infections can be demonstrated by following the incorporation of [$^3$H]-hypoxanthine (Desjardins, et al, (1979) *Antimicrobial Agents Chemotherapy* 16, 710–718) into drug-resistant *Plasmodium falciparum* using standard techniques. *P. falciparum* (clone D6, chloroquine-sensitive; strain FCR3, chloroquine-resistant; and clone W2, multidrug-resistant) was grown in vitro by the method of Trager and Jensen, (1976) *Science* 193, 673–675.

Table 1 illustrates the ability of compounds of this invention to enhance the potency of chloroquine against *P. falciparum* (FCR3). Dose-response curves and IC$_{50}$'s for chloroquine were determined either in the absence of compounds of this invention or in the presence of a fixed concentration of those compounds of 200 ng/ml. Addition of these compounds shifted the dose-response curves to the left, thus indicating that these compounds enhanced the potency of chloroquine.

wherein $R_1$ is methylene, n is 1, p is 0, q is 0 or 1, X is methyl or methoxy, and $R_2$ is methyl and $R_3$ is hydrogen or methyl. Most preferred are the compounds of formula (1) wherein $R_1$ is methylene, n is 1, p is 0, q is 0 or 1, X is methoxy, $R_2$ is methyl, and R is hydrogen or methyl.

The compounds
cis-2,3-dihydro-N,N-dimethyl-1-(phenylthio)-1H-indene-2-methanamine, ethanedioate;
cis-2,3-dihydro-1-(2-methoxyphenoxy)-N-methyl-1H-indene-2-methanamine;
cis-2,3-dihydro-N,N-dimethyl-1-[4-(trifluoromethyl)-phenoxy]-1H-indene-2-methanamine hydrochloride; and
2,3-dihydro-N,N-dimethyl-1-phenoxy-1H-indene-2-methanamine are exemplary of the preferred compounds of formula (1).

The following examples serve to illustrate synthetic procedures utilized to make compounds of formula (1) and pharmaceutical compositions containing compounds of this invention. These examples are intended to be illustrative only and are not intended to limit the invention in any way. All temperatures are in degrees Celsius.

EXAMPLE 1

CIS-2,3-dihydro-1-(2-methoxyphenoxy)-N,N-dimethyl-1H-indene-2-methanamine

STEP A;
CIS-2,3-Dihydro-2-(N,N-dimethylaminomethyl)-inden-1-ol

To an ice-cooled suspension of 2.25 g (0.01 M) of 2,3-dihydro-2-(N,N-dimethylaminomethyl)-1H-inden-1-one hydrochloride in 50 ml of dry tetrahydrofuran was added 25 ml of a 1 M solution of L-Selectride ®. The mixture was stirred for 1.5 hours and decomposed with 5 ml of 10% sodium hydroxide solution. The solvent was evaporated at reduced pressure and the residue distributed between ether and water. The ether layer was separated and extracted with dilute hydrochloric acid. Basification of the acid extract gave an oil which was extracted into ethyl acetate. Evaporation and Kugelrohr distillation at 90°–100°/0.4 mm gave 0.92 g (48%) of amino alcohol.

Anal. Calcd for $C_{12}H_{17}NO$;

TABLE 1

| Formula (1) Compound | | | | | | | | Stereo-chemistry | IC$_{50}$ of Chloroquine | Percent of Chloroquine Alone |
|---|---|---|---|---|---|---|---|---|---|---|
| n | p | q | X | $R_1$ | $R_2$ | $R_3$ | $R_4$ | | | |
| 1 | 0 | 0 | — | —CH$_2$— | CH$_3$ | CH$_3$ | S | cis | 8[1] | 14 |
| 1 | 0 | 1 | O—OCH$_3$ | —CH$_2$— | CH$_3$ | H | O | — | 7[1] | 13 |
| 1 | 0 | 1 | O—CF$_3$ | —CH$_2$— | CH$_3$ | H | O | cis | 12.5[1] | 22 |
| 1 | 0 | 1 | p-CF$_3$ | —CH$_2$— | CH$_3$ | H | O | (−) cis | 13[1] | 23 |
| 1 | 0 | 2 | m,p-(Cl)$_2$ | —CH$_2$— | CH$_3$ | CH$_3$ | O | trans | 24[1] | 43 |
| 1 | 0 | 1 | p-CF$_3$ | —CH$_2$— | CH$_3$ | CH$_3$ | O | cis | 31[1] | 55 |
| 1 | 0 | 1 | p-Br | —CH$_2$— | CH$_3$ | CH$_3$ | O | cis | 38[1] | 68 |
| 1 | 0 | 1 | p-CF$_3$ | —CH$_2$— | CH$_3$ | H | O | (+) cis | 33[1] | 59 |
| 1 | 0 | 2 | —OCH$_2$O— | —CH$_2$— | CH$_3$ | CH$_3$ | O | trans | 45[2] | 75 |
| 1 | 0 | 2 | —OCH$_2$O— | —CH$_2$— | CH$_3$ | CH$_3$ | O | cis | 15[2] | 25 |
| 1 | 0 | 0 | — | —CH$_2$— | CH$_3$ | CH$_3$ | O | — | 6[2] | 10 |

[1]Chloroquine only IC$_{50}$ = 56
[2]Chloroquine only IC$_{50}$ = 60

Compounds of formula (1) wherein $R_1$ is methylene are preferred. Also preferred are compounds of formula (1) wherein n is 1 as well as wherein X is lower alkyl, lower alkoxy or CF$_3$, wherein $R_2$ is methyl and $R_3$ is hydrogen or methyl, wherein y is O and wherein q is 0 or 1. More preferred are compounds of formula (1)

C=75.35; H=8.96,; N=7.32;
Fd: C=74.86; H=9.00; N=7.25;

By procedures analogous to that described above, the following amino alcohols can be prepared:

CIS-2,3-dihydro-2-(N-methyl-N-phenylmethylamino)-methyl-1H-inden-1-ol
Bp 135°-140°/0.3 mm
Anal. Calcd for $C_{18}H_{21}NO$;
C=80.86; H−7.92; N−5.24;
Fd: C=80.68; H=7.95; N=5.21;

CIS-6-chloro-2,3-dihydro-2-(N,N-dimethylamino)-methyl-1H-inden-1-ol
Bp 118°-121°/0.3 mm;
Anal. Calcd for $C_{12}H_{16}ClNO$;
C=63.85; H=7.15; N=6.21;
Fd: C=63.80; H=7.30; N=6.31;

CIS-2,3-dihydro-6-methoxy-2-dimethylaminomethylinden-1-ol
Bp 102°-110°/0.3 m;
Anal. Calcd for $C_{13}H_{15}NO_2$;
C=70.55; H−8.66; N=6.33;
Fd: C=70.23; H=8.86; N=6.20;

CIS-2,3-dihydro-6-fluoro-2-dimethylaminomethylinden-1-ol
Bp 90°-93°/0.3 m;
Anal. Calcd. for $C_{12}H_{16}FNO$;
C=68.87; H=7.71; N=6.60;
Fd: C=68.82; H=7.82; N=6.52;

CIS-2,3-dihydro-5-fluoro-2-(N,N-diethylamino)methyl-1H-inden-1-ol

CIS-2,3-dihydro-3,3-dimethyl-2-(N,N-dimethylamino)-methyl-6-methoxy-1H-inden-1-ol CIS-2,3-dihydro-2-(N-ethyl-N-methylamino)methyl)-5,6-dimethoxy-1H-inden-1-ol CIS-6-(N,N-dimethylamino)methyl-5,6,7,8-tetrahydrobenzocycloheptene-5-ol CIS-2,3-dihydro-2-(N,N-dimethylamino)ethyl-1H-inden-1-ol CIS-2-diethylamino-1,2,3,4-tetrahydronaphthalene-1-ol CIS-2-(dimethylamino)methyl-1,2,3,4-tetrahydronaphthalen-1-ol TRANS-2-dimethylaminomethyl-1,2,3,4-tetrahydronaphthalen-1-ol
Bp 127°-35°/0.4 mm
Anal. Calcd for $C_{13}H_{19}NO$;
C=76.05; H=9.33; N=6.82;
Fd: C=75.83; H=9.21; N=6.50;

The following compounds were prepared utilizing sodium borohydride as the reducing agent rather than Selectride TM.

TRANS-2,3-dihydro-2-dimethylaminomethyl-inden-1-ol
m.p. 65°-67°
Anal. Calcd. for $C_{12}H_{17}NO$;
C=75.35; H=8.96; N=7.32;
Fd: C=75.32; N=8.96; N=7.26

TRANS-2,3-dihydro-6-fluoro-2-dimethylaminomethyl-inden-1-ol
m.p. 93°-95°
Anal. Calcd. for $C_{12}H_{16}FNO$;
C=68.87; H=7.71; N=6.69;
Fd: C=69.02; H=7.84; N=6.57;

STEP B:

CIS-2,3-dihydro-1-(2-methoxyphenoxy)-N,N-dimethyl-1H-indene-2-methanamine

A mixture of 0.75 g of 50% sodium hydride dispersion in oil and 10 ml of dimethylsulfoxide was heated in an oil bath at 65° in a nitrogen atmosphere for 30 minutes and cooled to room temperature. CIS-2,3-dihydro-2-(N,N-dimethylamino-methyl)-inden-1-ol (1.91 g, 0.01 M) was added and the mixture stirred for 15 minutes.

2-Fluoroanisole (3.5 ml) was added and the mixture heated at 90° overnight. After cooling and diluting with water, the product was extracted into ethyl acetate. The amine was isolated by chromatography on silica and elution with 10% ethyl acetate in hexane. Kugelrohr distillation at 123°-125°/0.4 mm gave the pure amine.

Anal. Calcd. for $C_{19}H_{23}NO_2$:
C=76.73; H−7.80; N−4.71
Fd: C=76.62; H=7.99; N=4.98

By procedures analogous to that described above, the following compounds of the formula (1) can be prepared:

CIS-2,3-dihydro-N,N-dimethyl-1-phenoxy-1H-indene-2-methanamine
Bp 110°-115°/0.3 mm
Anal. Calcd for $CC_{18}H_{21}NO$:
C=80.86; H=7.92; N=5.24;
Fd: C=80.58; H=7.93; N=5.01

CIS-2,3-dihydro-N,N-dimethyl-1-(4-trifluoromethyl-phenoxy)-1H-indene-2-methanamine hydrochloride
mp 178°-180°
Anal. Calcd for $C_{19}H_{20}F_3NO \cdot HCl$ CIS-2,3-dihydro-N-methyl-1-(2-trifluoromethyl-phenoxy)-H-indene-2-methanamine ethanedioate (1:1)
mp 194°-195° C.
C=61.37; H=5.69; N=3.77;
Fd: C=61.23; H=5.79; N=3.70

CIS-1,2,3,4-tetrahydro-1-(2-methoxyphenoxy)-N,N-dimethyl-2-naphthalenemethanamine
Bp 135°-140°/0.4 mm
Anal. Calcd for $C_{20}H_{25}NO_2$:
C=77.13; H=8.09; N−4.50;
Fd: C=77.02; H=8.05; N=4.52

CIS-1-(3,4-dichlorophenoxy)-2,3-dihydro-N,N-dimethyl-1H-indene-2-methanamine hydrochloride
mp 192°-193°
Anal. Calcd for $C_{18}H_{19}Cl_2NO \cdot HCl$:
C=58.00; H=5.41; N−3.76;
Fd: C=58.11; H=5.49; N=3.68

CIS-6-chloro-2,3-dihydro-1-(2-methoxyphenoxy)-N,N-dimethyl-1H-indene-2-methanamine maleate
mp 141°-143°
Anal. Calcd. for $C_{19}H_{22}ClNO_2 \cdot C_4H_4O_4$;
C=61.67; H=5.85; N=3.13;
Fd: C=61.39; H=5.97; N=3.01

CIS-2,3-dihydro-N,N-dimethyl-1-(2-methylphenoxy)-1H-indene-2-methanamine oxalate CIS-2,3-dihydro-N,N-dimethyl-1-phenoxy-1H-indene-2-amine CIS-2,3-dihydro-1-(3,4-dimethoxyphenoxy)-N,N-dimethyl-1H-indene-2-methanamine CIS-5-(4-fluorophenoxy)-5,6,7,8-tetrahydrobenzocyclo-hepten-6-methanamine CIS-1-(3-chlorophenoxy)-2,3-dihydro-3,3,N,N-tetramethyl-6-methoxy-1H-indene-2-methanamine CIS-1-(4-romophenoxy)-2,3-dihydro-N,N-dimethyl-1H-indene-2-methanamine ethanedioate
mp 189°-190° C.

CIS-2,3-dihydro-1-(2-ethoxyphenoxy)-N-methyl-1H-indene-2-methanamine,
bp 135°-140° C. (0.3 mm Hg)

EXAMPLE 2

CIS and TRANS-1,2,3,4-tetrahydro-1-(2-methoxyphenoxy)-N,N-dimethyl-2-naphthalenemethanamine A mixture of 8.21 g (0.04 M) of TRANS-1,2,3,4-tetrahydro-2-(N,N-dimethylaminomethyl)naphthalen-1-ol, 11.54 triphenyl phosphine, 5.46 g (0.044 M) of triphenyl phosphine, 5.46 g (0.044 M) of 2-methoxyphenol and 100 ml of benzene was stirred and a solution of 7.83 g (0.004 M) of 95% diethyl azodicarbox-ylate in 25 ml of benzene was added dropwise over 45 minutes. After 2 hours, the mixture was filtered and extracted with cold 3% hydrochloric acid. The acid extracts were made basic with dilute sodium hydroxide and the oil which separated was extracted into ether. The solvent was removed and the residual oil chromatographed on silica gel.

Elution with 1:1 ether-chloroform gave the TRANS-isomer—1.20 g, Bp 135°-38°/0.4 mm.

Anal. Calcd for $C_{20}H_{25}NO_2$: C=77.13; H=8.09; N—4.50:

Fd: C=77.15; H=8.21; N=4.56

Elution with ether gave the CIS-isomer, 2.64 g. Bp 135°-40°/0.4 mm

Anal Calcd. for $C_{20}H_{25}NO_2$: C=77.13; H=8.09; N=4.50;

Fd: C=77.02; H=8.05; N=4.52.

EXAMPLE 3

CIS and TRANS-2,3-dihydro-1-(2-methoxyphenoxy)-N,N-dimethyl-1H-inden-2-amine oxalate A mixture of 1.0 g sodium hydride (50% suspension in oil) and 25 ml of dimethylsulfoxide was heated in an oil bath at 60° for 0.5 hours. The mixture was cooled and 2.22 g (0.013 m) of CIS-2,3-dihydro-2-N,N-dimethylamino-1H-inden-1-ol was added. After stirring 10 minutes, 3.3 g (0.026 M) of 2-fluoroanisol was added and the mixture heated at 90° for 21 hours. After cooling, the mixture was poured into water and extracted with ethyl acetate. Evaporation left an oil which was chromatographed on silica gel. Elution with ethyl acetate gave the TRANS-isomer which was converted into the oxalate salt in ether (0.72 g, m.p. 172°-73°).

Anal. Calcd. for $C_{18}H_{21}NO_2 \cdot C_2H_2O_4$:
C=64.33; H—6.21; N=3.75;

Fd: C=64.23; H=6.29; N=3.72

The CIS isomer was eluted with 9:1 ethyl acetate-methanol and converted to the oxalate salt in ether—0.92 g, m.p. 149°-50°

Fd: C=64.16; H=6.27; N=3.80

The starting materials for the above reaction scheme, i.e., the appropriately substituted amino ketones (2) and aryl fluoride/alcohols, are readily obtained through the use of commonly available reagents modified if required through standard synthetic schemes, procedures and techniques as are well known and appreciated by those of ordinary skill in the art.

For example, the appropriate amino alcohol intermediate for compounds of the formula (1) wherein n is O can be prepared by procedures analogous to that described by Huebner, et al, [J. Org. Chem. 35, 1149 (1970)].

The appropriate amino ketone starting material for compounds of the formula (1) wherein n is O, 1 or 2 can be prepared by procedures analogous to that described in U.S. Pat. No. 2,947,756.

EXAMPLE 4

TRANS, CIS-2,3-dihydro-N,N-dimethyl-(1-phenylthio)inden-2-methylamine

A mixture of 4.54 g (0.02 m) TRANS-2,3-dihydro-2-N,N-dimethylaminomethylinden-1-ol, 4.80 g (0.022 m) of diphenyl disulfide and 4.45 g (0.022 m) of tri-n-butylphosphine in 50 1 of dry benzene was stirred at room temperature overnight. The solvent was removed at reduced pressure and the product isolated by flash chromatography. Elution with 5% methanol in ethyl acetate gave first the TRANS isomer which was purified as the oxalate salt, mp 189°-191° C.

Anal. Calcd. for $C_{18}H_{21}NS \cdot C_2H_2O_4$: C=64.32; H=6.21; N=3.75;

Fd: C=63.54; H=6.22; N=3.66

Continued elution gave fractions of the pure CIS isomer which was purified as the oxalate salt, mp 113°-116° C.

Fd: C=64.00; H=6.30; N=3.64.

Also prepared in an analogous manner were CIS and TRANS 1-(1,3-benzodioxol-5-yloxy)-2,3-dihydro-N,N-dimethyl-1H-indene-2-methanamine ethanedioate (1:1).

mp 185°-186° C. (CIS isomer)
mp 165°-167° C. (TRANS isomer).

We claim:

1. A method of reversing drug-resistance in a patient having a drug-resistant malarial infection which comprises administering to the patient a drug-resistance reversing amount of a compound of the formula wherein
   $R_1$ is a $C_1$-$C_3$ alkylene,
   n, p and q are each independently 0, 1 or 2,
   Y and X are each independently lower alkyl, lower alkoxy, hydroxy, $CF_3$, halogeno or when p or q are 2 and each of the Y or each of the X groups are on adjacent aryl carbon atoms, both of the X or both of the Y groups can be taken together to form a methylene dioxy moiety,
   $R_2$ and $R_3$ are each independently hydrogen or lower alkyl, $R_4$ is an oxy or thio,
or an acid addition salt thereof.

2. A method of claim 1 wherein $R_2$ is methyl and $R_3$ is hydrogen.

3. A method of claim 1 wherein $R_2$ and $R_3$ are each methyl.

4. A method of claim 1 wherein $R_1$ is —$CH_2$— or —$CH_2CH_2$—.

5. A method of claim 1 wherein n is 1.

6. A method of claim 1 wherein p is O.

7. A method of claim 1 wherein Y is chloro and p is 1.

8. A method of claim 1 wherein X is CF$_3$ and q is 1.

9. A method of claim 1 wherein X is methoxy and q is 1.

10. A method of claim 1 wherein q is O.

11. A method of claim 1 wherein X is chloro and q is 1.

12. A method of claim 1 wherein R$_4$ is oxy.

13. A method of claim 1 wherein the drug-resistant malarial infection is a chloroquine-resistant material infection.

* * * * *

UNITED STATES PATENT AND TRADEMARK OFFICE
CERTIFICATE OF CORRECTION

PATENT NO.  : 5,134,168
DATED       : July 28, 1992
INVENTOR(S) : Alan J. Bitonti and Jules Freedman It is certified that error appears in the above-identified patent and that said Letters Patent is hereby corrected as shown below:

At Column 2, line 28, the patent reads "CF," and should read --CF$_3$,--.

At Column 4, line 5, the patent reads "thereof" and should read --thereof.--.

At Column 5, line 55, the patent reads "methanolethyl" and should read --methanol:ethyl--.

At Column 10, lines 27 and 28, the patent reads "dimethYl-" and should read --dimethyl---.

At Column 12, line 62 the patent reads "romophenoxy" and should read --bromophenoxy--.

At Column 13, lines 8 and 9, the patent reads "11.54 triphenyl phosphine, 5.46 g (0.044 M) of triphenyl phosphine, 5.46 g (0.044 M)" and should read --11.54 g (0.044 M) of triphenyl phosphine, 5.46 g (0.044 M)--

At Column 16, line 5, the patent reads "material" and should read --malarial--.

Signed and Sealed this

Thirteenth Day of September, 1994

Attest:

BRUCE LEHMAN

*Attesting Officer*    *Commissioner of Patents and Trademarks*